US009823249B2

(12) United States Patent
Demirci et al.

(10) Patent No.: US 9,823,249 B2
(45) Date of Patent: Nov. 21, 2017

(54) SYSTEM AND METHOD FOR DETECTING PATHOGENS

(71) Applicants: Utkan Demirci, Cambridge, MA (US); Hadi Shafiee, Cambridge, MA (US)

(72) Inventors: Utkan Demirci, Cambridge, MA (US); Hadi Shafiee, Cambridge, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 9 days.

(21) Appl. No.: 14/651,589

(22) PCT Filed: Dec. 12, 2013

(86) PCT No.: PCT/US2013/074701
§ 371 (c)(1),
(2) Date: Jun. 11, 2015

(87) PCT Pub. No.: WO2014/093639
PCT Pub. Date: Jun. 19, 2014

(65) Prior Publication Data
US 2015/0309024 A1    Oct. 29, 2015

Related U.S. Application Data

(60) Provisional application No. 61/736,174, filed on Dec. 12, 2012, provisional application No. 61/885,244, filed on Oct. 1, 2013.

(51) Int. Cl.
G01N 33/569    (2006.01)
C12N 1/02    (2006.01)
(Continued)

(52) U.S. Cl.
CPC ...... G01N 33/56988 (2013.01); B01L 3/5023 (2013.01); B01L 3/5027 (2013.01);
(Continued)

(58) Field of Classification Search
CPC ......... G01N 33/56988; G01N 33/5438; G01N 27/3275; B01L 3/5023; B01L 3/502707; B01L 3/5027
See application file for complete search history.

(56) References Cited

U.S. PATENT DOCUMENTS 6,586,253 B1 *   7/2003   Harrison ............... C12Q 1/34
                                                     422/504
9,233,370 B2 *   1/2016   Miller ............... B01L 3/502761
(Continued)

OTHER PUBLICATIONS

Aldaeus, et al., Superpositioned Dielectrophoresis for Enhanced Trapping Efficiency, Electrophoresis, 2005, 26(22):4252-4259.
(Continued)

Primary Examiner — Melanie Y Brown
(74) Attorney, Agent, or Firm — Quarles & Brady LLP

(57) ABSTRACT

A method of detecting a pathogen in a sample. The pathogen from the sample is captured with at least one recognition element. The sample is introduced to a paper-based microfluidic device having spaced electrodes disposed thereon. An impedance magnitude of the sample is measured across the spaced electrodes to detect a presence of the pathogen in the sample. A related paper-based microfluidic device and system are also disclosed.

8 Claims, 14 Drawing Sheets

(51) Int. Cl.

| | |
|---|---|
| G01N 33/543 | (2006.01) |
| B01L 3/00 | (2006.01) |
| C07K 16/10 | (2006.01) |
| G01N 27/327 | (2006.01) |
| C12M 1/34 | (2006.01) |

(52) U.S. Cl.
CPC .... *B01L 3/502707* (2013.01); *C07K 16/1063* (2013.01); *C12N 1/02* (2013.01); *G01N 27/3275* (2013.01); *G01N 33/5438* (2013.01); *B01L 2200/10* (2013.01); *B01L 2300/0645* (2013.01); *B01L 2300/0816* (2013.01); *B01L 2300/126* (2013.01); *C12M 41/36* (2013.01); *C12Q 2565/629* (2013.01)

(56) References Cited

U.S. PATENT DOCUMENTS

| | | | |
|---|---|---|---|
| 2002/0090649 A1* | 7/2002 | Chan | B01J 19/0046 435/7.1 |
| 2002/0150886 A1 | 10/2002 | Miles et al. | |
| 2002/0197622 A1* | 12/2002 | McDevitt | G01N 33/54373 435/6.12 |
| 2005/0208592 A1* | 9/2005 | Caron | G01N 33/54373 435/7.1 |
| 2008/0261197 A1* | 10/2008 | Charneau | C07K 14/005 435/5 |
| 2009/0068638 A1* | 3/2009 | Shabani | G01N 33/56911 435/5 |
| 2010/0123457 A1* | 5/2010 | Shinoda | B01L 3/502753 324/228 |
| 2011/0053144 A1* | 3/2011 | Garcia Aljaro | C12Q 1/6825 435/5 |
| 2011/0086352 A1* | 4/2011 | Bashir | C12Q 1/6825 435/6.11 |
| 2011/0272281 A1* | 11/2011 | Plecis | G01N 27/44752 204/451 |
| 2012/0122731 A1* | 5/2012 | Soh | B01L 3/502761 506/12 |
| 2012/0167988 A1 | 7/2012 | Wang et al. | |
| 2012/0181184 A1* | 7/2012 | Whitesides | B01L 3/502 205/775 |
| 2013/0037998 A1* | 2/2013 | Dogan | G06F 17/504 264/614 |
| 2013/0295588 A1* | 11/2013 | Watkins | C12M 41/36 435/7.24 |
| 2014/0001058 A1* | 1/2014 | Ghaffari | G01N 27/327 205/792 |

OTHER PUBLICATIONS

Asami, Characterization of Heterogeneous Systems by Dielectric Spectroscopy, Progress in Polymer Science, 2002, 27(8):1617-1659.

Balakrishnan, et al., Low-Cost Assays for Monitoring HIV Infected Individuals in Resource-Limited Settings, Indian J. Med. Res., 2011, 134:823-834.

Chang, et al., Electrochemical Impedance Spectroscopy, Annu. Rev. Anal. Chem., 2010, 3:207-229.

Chen, et al., Concentration and Purification of Human Immunodeficiency Virus Type 1 Virions by Microfluidic Separation of Superparamagnetic Nanoparticles, Analytical Chemistry, 2010, 82(2):723-728.

Cheng, et al., Cell Detection and Counting Through Cell Lysate Impedance Spectroscopy in Microfluidic Devices, Lab on a Chip, 2007, 7(6):746-755.

Cheung, et al., Impedance Spectroscopy Flow Cytometry: On-Chip Label-Free Cell Differentiation, Cytometry Part A, 2005, 65A:124-132.

Chin, et al., Microfluidics-Based Diagnostics of Infectious Diseases in the Developing World, Nature Medicine, 2011, 17(8):1015-1019.

Collins, et al., Microfluidic Flow Transducer Based on the Measurement of Electrical Admittance, Lab on a Chip, 2004, 4(Adance Article), 12 pages.

Cui, et al., Nanowire Nanosensors for Highly Sensitive and Selective Detection of Biological and Chemical Species, Science, 2001, 293:1289-1292.

Das, et al., Protein Detection Using Arrayed Microsensor Chips: Tuning Sensor Footprint to Achieve Ultrasensitive Readout of CA-125 in Serum and Whole Blood, Analytical Chemistry, 2011, 83(4):1167-1172.

Drosten, et al., Ultrasensitive Monitoring of HIV-1 Viral Load by a Low-Cost Real-Time Reverse Transcription—PCR Assay with Internal Control for the 5' Long Terminal Repeat Domain, Clinical Chemistry, 2006, 52(7):1258-1266.

Drummond, et al., Electrochemical DNA Sensors, Nature Biotechnology, 2003, 21:1192-1199.

Fricke, et al., Electric Impedance of Suspensions of Leucocytes, Nature, 1935, 135:436.

Inci, et al., Nanoplasmonic Quantitative Detection of Intact Viruses from Unprocessed Whole Blood, ACS Nano, 2013, 7(6):4733-4745.

Jangam, et al., A Point-Of-Care PCR Test for HIV-1 Detection in Resource-Limited Settings, Biosensors and Bioelectronics, 2013, 42:69-75.

Kim, et al., Fabrication of Comb Interdigitated Electrodes Array (IDA) for a Microbead-Based Electrochemical Assay System, Biosensors and Bioelectronics, 2004, 20(4):887-894.

Kim, et al., Quantum Dot-Based HIV Capture and Imaging in a Microfluidic Channel, Biosensors and Bioelectronics, 2009, 25:253-258.

Labib, et al., Towards an Early Diagnosis of HIV Infection: An Electrochemical Approach for Detection of HIV-1 Reverse Transcriptase Enzyme, Analyst, 2011, 136:708-715.

Lam, et al., Solution-Based Circuits Enable Rapid and Multiplexed Pathogen Detection, Nature Communications, 2013, 4, 8 pages.

Li, et al., Dielectrophoretic Separation and Manipulation of Live and Heat-Treated Cells of Listeria on Microfabricated Devices with Interdigitated Electrodes, Sensors and Actuators B, 2002, 86:215-221.

Lin, et al. Biogenic Nanoporous Silica-Based Sensor for Enhanced Electrochemical Detection of Cardiovascular Biomarkers Proteins, Biosensors and Bioelectronics, 2010, 25(10):2336-2342.

Lin, et al., Organic Thin-Film Transistors for Chemical and Biological Sensing, Advanced Materials, 2012, 24:34-51.

Liu, et al., Aptamer-Based Origami Paper Analytical Device for Electrochemical Detection of Adenosine, Angew. Chem. Int. Ed. Engl., 2012, 51(28):6925-6928.

Luo, et al., Electrical Biosensors and the Label Free Detection of Protein Disease Biomarkers, Chemical Society Reviews, 2013, 42:5944-5962.

Mahalanabis, et al., An Integrated Disposable Device for DNA Extraction and Helicase Dependent Amplification, Biomed Microdevices, 2010, 12(2):353-359.

Malhotra, et al., Ultrasensitive Electrochemical Immunosensor for Oral Cancer Biomarker IL-6 Using Carbon Nanotube Forest Electrodes and Multilabel Amplification, Anal. Chem., 2010, 82(8):3118-3123.

Mani, et al., Ultrasensitive Immunosensor for Cancer Biomarker Proteins Using Gold Nanoparticle Film Electrodes and Multienzyme-Particle Amplification, ACS Nano, 2009, 3(3):585-594.

Martinez, et al., Patterned Paper as a Platform for Inexpensive, Low Volume, Portable Bioassays, Angew. Chem. Int. Ed. Engl., 2007, 46(8):1318-1320.

Martinez, et al., Diagnostics for the Developing World: Microfluidic Paper-Based Analytical Devices, Analytical Chemistry, 2010, 82:3-10.

Mee, et al., Evaluation of the WHO Criteria for Antiretroviral Treatment Failure Among Adults in South Africa, AIDS, 2008, 22:1971-1977.

Mermin, et al., Utility of Routine Viral Load, CD4 Cell Count, and Clinical Monitoring Among Adults with HIV Receiving Antiretroviral Therapy in Uganda: Randomised Trial, BMJ, 2011, 343:d6792, 11 pages.

(56) References Cited

OTHER PUBLICATIONS

Moon, et al., Integrating Microfluidics and Lensless Imaging for Point-Of-Care Testing, Biosensors and Bioelectronics, 2009, 24(11):3208-3214.
Moore, et al., Performance of Immunologic Responses in Predicting Viral Load Suppression, J. Acquir. Immune Defic. Syndr., 2006, 43(4):436-439.
Morgan, et al., Separation of Submicron Bioparticles by Dielectrophoresis, Biophysical Journal, 1999, 77:516-525.
Nebling, et al., Electrical Detection of Viral DNA Using Ultramicroelectrode Arrays, Analytical Chemistry, 2004, 76(3):689-696.
Nie, et al., Electrochemical Sensing in Paper-Based Microfluidic Devices, Lab on a Chip, 2010, 10:477-483.
Patolsky, et al., Electrical Detection of Single Viruses, PNAS, 2004, 101(39):14017-14022.
Ronkainen, et al., Electrochemical Biosensors, Chemical Society Reviews, 2010, 39:1747-1763.
Rosenberg, et al., Detection of Acute HIV Infection: A Field Evaluation of the Determine(R) HIV-1/2 Ag/Ab Combo Test, Journal of Infectious Diseases, 2012, 205:528-534.
Shafiee, et al., Acute On-Chip HIV Detection Through Label-Free Electrical Sensing of Viral Nano-Lysate, Small, 2013, 9(15):2553-2563.
Sohn, et al., Capacitance Cytometry: Measuring Biological Cells One by One, PNAS, 2000, 97(20):10687-10690.
Song, et al., Functional Nanoprobes for Ultrasensitive Detection of Biomolecules, Chemical Society Reviews, 2010, 39:4234-4243.
Tang, et al., Ultrasensitive Electrochemical Immunosensor for Clinical Immunoassay Using Thionine-Doped Magnetic Gold Nanospheres as Labels and Horseradish Peroxidase as Enhancer, Analytical Chemistry, 2008, 80:1582-1588.
Tanriverdi, et al., A Rapid and Automated Sample-To-Result HIV Load Test for Near-Patient Application, Journal of Infectious Diseases, 2010, 201(S1):S52-S58.
Usdin, et al., Patient Needs and Point-Of-Care Requirements for HIV Load Testing in Resource-Limited Settings, Journal of Infectious Diseases, 2010, 201(S1):S73-S77.
Varshney, et al., Interdigitated Array Microelectrodes Based Impedance Biosensors for Detection of Bacterial Cells, Biosensors and Bioelectronics, 2009, 24:2951-2960.
Varshney, et al., A Label-Free, Microfluidics and Interdigitated Array Microelectrode-Based Impedance Biosensor in Combination with Nanoparticles Immunoseparation for Detection of *Escherichia coli* O157:H7 in Food Samples, Sensors and Actuators B, 2007, 128(1):99-107.
Wang, et al., Advances in Developing HIV-1 Viral Load Assays for Resource-Limited Settings, Biotechnol. Adv., 2010, 28(6):770-781.
Wang, et al., Efficient On-Chip Isolation of HIV Subtypes, Lab on a Chip, 2012, 12(8):1508-1515.
World Health Organization, Guidance on Provider-Initiated HIV Testing and Counselling in Health Facilities, Copyright World Health Organization 2007, 60 pages.
Yager, et al., Microfluidic Diagnostic Technologies for Global Public Health, Nature, 2006, 442:412-418.
Yang, et al., Interdigitated Array Microelectrode-Based Electrochemical Impedance Immunosensor for Detection of *Escherichia coli* O157:H7, Analytical Chemistry, 2004, 76(4):1107-1113.
Zhang, et al., Survey and Summary—Miniaturized PCR Chips for Nucleic Acid Amplification and Analysis: Latest Advances and Future Trends, Nucleic Acids Research, 2007, 35(13):4223-4237.
Zhang, et al., Insulin Oxidation and Determination at Carbon Electrodes, Analytical Chemistry, 2005, 77:6396-6401.
Zuo, et al., High Specificity, Electrochemical Sandwich Assays Based on Single Aptamer Sequences and Suitable for the Direct Detection of Small-Molecule Targets in Blood and Other Complex Matrices, J. Am. Chem. Soc., 2009, 131(20):6944-6945.
PCT International Search Report and Written Opinion, PCT/US2013/074701, dated Apr. 27, 2014.

* cited by examiner

SYSTEM AND METHOD FOR DETECTING PATHOGENS

CROSS-REFERENCE TO RELATED APPLICATIONS

This application represents the U.S. National Stage of International Application No. PCT/US2013/074701, filed Dec. 12, 2013 which claims the priority benefit of U.S. provisional patent application Ser. No. 61/736,174 filed Dec. 12, 2012 and U.S. provisional patent application No. 61/885,244 filed on Oct. 1, 2013. The contents of those applications are incorporated by reference for all purposes as if set forth in their entirety herein.

STATEMENT REGARDING FEDERALLY SPONSORED RESEARCH

Not applicable.

BACKGROUND OF THE INVENTION

This invention relates to systems and methods for the detection of pathogens. More particularly, the invention relates to paper-based microfluidic systems for pathogen detection.

Antiretroviral therapy (ART) as a successful treatment to suppress human immunodeficiency virus (HIV), prolong life in HIV-infected patients, and reduce HIV infection transmission rates has become even more affordable and accessible in many developing countries. However, a majority of HIV-infected individuals do not receive ART (46% of HIV-infected patients by the end of 2011) due to lack of affordable, rapid, and sensitive HIV diagnostic tools at the point-of-care (POC).

CD4 cell count and clinical symptoms have been used to initiate and guide ART in developing countries. According to the WHO guidelines, ART is initiated when CD4+ cells fall below 350/μL with WHO Stage II or WHO clinical Stage III and IV irrespective of CD4 cell count. It has been reported that recommended clinical symptoms criteria might lead to false positive diagnosis when compared with virological criteria. CD4 cell counting strategy alone is not sufficient to monitor patients efficiently or detect early virological failure, which allow for accumulation of drug-resistant strains and reduce the efficacy of second-line ART regimens and consequently shortening the clinical durability of available ART in developing countries.

The early detection of virological failure allows for both targeted adherence interventions as well as better preservation of the efficacy of second-line regimens. Without virological failure confirmation, HIV health care providers may prescribe switching to premature second-line ART and more complex antiretroviral regimen. Virological suppression, however, represents a more accurate immunological response of the patient to ART. Therefore, for an improved accurate diagnosis of treatment failure and to expand access to ART, emerging technologies to facilitate viral load testing at the POC are urgently needed. POC viral load testing may lead to increasing the adherence and minimizing the drug resistance through timely detection of virological failure and converting of failing regimens.

Several technologies have been used to develop viral load methods such as ELISA (ExaVir™), reverse transcriptase polymerase chain reaction (RT-PCR) (Liat™ analyzer), ultrasensitive p24 assay, microfluidic nucleic acid amplification, miniaturized PCR, microfluidics and quantum dots, and nanoplasmonic detection on self-assembled gold nanoparticles. Although, these assays offer promising methods for viral load measurements, they are either in the development process, are relatively expensive, require air conditioning, and/or require skilled operators.

Therefore, current viral load technologies are not suitable for POC testing in resource-constrained settings. Thus, to increase access to ART, a rapid, inexpensive, and simple viral load test is urgently needed at the POC.

SUMMARY OF THE INVENTION

The present invention overcomes the aforementioned drawbacks by providing a system and related method of detecting a pathogen in a sample using a paper-based microfluidic device.

Diagnostic devices for infectious diseases detection and treatment monitoring in resource-constrained settings should be affordable, sensitive, specific, user-friendly, rapid and robust, equipment free, and deliverable to end-users (ASSURED) according to World Health Organization (WHO) guidelines. The combination of electrical sensing and paper-based microfluidics described below offers a promising opportunity to create such diagnostic tools for developing world. A portable paper-based microchip platform has been developed with simple and mass-producible fabrication technology that can selectively capture and detect HIV-1 utilizing impedance spectroscopy of viral lysate. Multiple HIV subtypes at clinically relevant viral loads that occur during the seroconversion stage (acute HIV) were detected in biological samples including whole blood and plasma using this microchip technology. The specificity of the microchip was also evaluated in the presence of a non-HIV virus (EBV) and the results were evaluated using reverse transcriptase quantitative polymerase chain reaction (RT-qPCR) method as the gold standard method for viral load measurement in developed countries.

Electrical sensing of small biomolecules, proteins, DNA, and pathogens in biological samples including whole blood, plasma, and sputum has offered a sensitive, specific, and robust diagnostic method for a variety of diseases including cancer and infectious diseases. Paper-based microfluidics has also opened an exciting and promising avenue in the area of diagnostics at the POC. Paper-based microchips are inexpensive, easy to fabricate, mass-producible, easy-to-use, and disposable. Paper is readily available around the world and a paper-based microchip can be made for less than one cent. Paper is thin, light (approximately 10 mg/cm$^2$) and flexible and can absorb fluid samples through capillary effect. Therefore, paper-based microfluidics is a new attractive method for developing affordable tools for broad applications such as drug development, monitoring water and environment quality, and infectious diseases diagnostic at the POC in resource-constrained settings.

In this application, paper-based microfluidic technology has been integrated with electrical sensing to develop an inexpensive, rapid, and disposable microchip for virus detection at the POC. Multiple HIV-1 subtypes (A, B, C, D, E, G, and panel) have been successfully captured and detected utilizing impedance spectroscopy of viral lysate on a paper-based microfluidic device. The microchip has demonstrated the ability to detect HIV at viral loads ($10^6$-$10^8$ copies/mL) that occur at the early stage of the infection (acute HIV) where current rapid POC tests and ELISA methods such as OraQuick® cannot detect. This microchip technology is shown to detect HIV-1 spiked in whole blood and plasma samples with viral loads between $10^6$ and $10^8$ copies/mL. This method offers a simple, rapid, and broadly applicable technology to detect pathogens and viruses such as pox, hepatitis, influenza, and tuberculosis in biological samples including whole blood and plasma.

According to one aspect of the invention, a method of detecting a pathogen in a sample is disclosed. The pathogen is captured from the sample with one or more recognition elements. For example, these recognition element(s) may be disposed on magnetic beads or, as another example, the surface of a microchip may be functionalized with the recognition element(s). The sample is introduced to a paper-based microfluidic device having spaced electrodes disposed thereon. An impedance magnitude of the sample is measured across the spaced electrodes to detect a presence of the pathogen in the sample.

In some forms, the sample may be blood or plasma, the pathogen may be a virus, and the recognition element may be an antibody. In one specific form, the recognition element(s) may be found on magnetic beads conjugated with the recognition element(s). As one specific example, streptavidin-coated magnetic beads may be conjugated with anti-gp-120 antibodies and the virus may be HIV-1. It is contemplated that other pathogens or viruses could be detected instead of HIV-1, although in such instances the recognition element(s) would be selected to match the entities being detected. Further, although anti-gp120 antibodies are used in the examples below to capture HIV-1, other antibodies such as anti-gp41 antibodies or a cocktail of these antibodies may be used to capture HIV-1.

The spaced electrodes may be, for example, silver or graphite so as to permit the measurements of an impedance magnitude. However, any conductive ink material may be used to fabricate the electrodes on paper-based devices. Silver and graphite inks are just examples of such materials. Further, it will be appreciated that 2D and 3D micro and macro fabrication technologies can be used to create the electrodes on paper-based microchips. For example, 3D printing technology can be utilized to fabricate electrodes with different geometries.

In some forms of the method, introducing the sample to the paper-based microfluidic device having the spaced electrodes disposed thereon may include introducing the sample to a microfluidic channel spanning the distance between the spaced electrodes. This might be done for example, by applying a drop of the sample (such as blood) to an opening of the microfluidic channel.

In some forms of the method, there may be other steps to help improve impedance measurement and improve detection accuracy. For example, after the step of capturing the pathogen from the sample with the recognition element(s), the sample may be washed to remove electrically conductive solution. Additionally, the pathogen may be lysed to release one or more electrically conductive chemical entities inside the pathogen after the step of capturing the pathogen from the sample with the recognition element(s). The one or more electrically conductive chemical entities may include one or more of ions, proteins, antigens, enzymes, and biomolecules inside the captured pathogen. In one specific form, Triton x-100 may be used to lyse the pathogen to release one or more electrically conductive chemical entities inside the pathogen.

In some forms of the method, measuring an impedance magnitude of the sample to detect the presence of the pathogen in the sample may include measuring an impedance magnitude of a control sample, measuring the impedance magnitude of the sample, and determining the change in impedance magnitude from the control sample to the sample to detect the presence of the pathogen in the sample. Although the impedance magnitude might be measured at a number of different frequencies and voltages, it was found that 1000 Hz and 1 V are particularly good parameters at which to measure impedance magnitude.

It is contemplated that in some forms of the method, that the detection of the pathogen may occur in the presence of another type of pathogen. In this way, the system may possess the ability to selectively detect the pathogen even in the presence of another type of pathogen.

According to another aspect of the invention, a paper-based microfluidic device is disclosed. The paper-based microfluidic device includes a substrate, spaced electrodes patterned on the paper substrate, and a microfluidic channel spanning the distance between spaced electrodes.

In some forms of the device, the substrate may be a hydrophobic transparency paper and the spaced electrodes may be silver (and patterned from silver ink) or may be graphite. Again, however, any conductive ink material might be used to form the electrodes and 2D or 3D microfabrication technology may be employed to fabricate these electrodes with different geometries.

It is contemplated that in some forms of the device, the paper-based microfluidic device may be flexible (including the electrodes).

According to still another aspect of the invention a system for detecting a pathogen in a sample according to the methods described above is disclosed. The system includes a paper-based microfluidic device including a substrate, spaced electrodes patterned on the substrate, and a microfluidic channel spanning the distance between the spaced electrodes for receiving the sample. The system further includes an electric device for measuring an impedance magnitude across the spaced electrodes in order to detect the presence of a pathogen in the sample.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6A illustrates average impedance magnitude and FIG. 6B illustrates phase spectra for lysed HIV-1 subtype A, Epstein-Barr virus (EBV), and mixture of HIV and EBV for frequencies between 100 Hz and 1 MHz. There was no virus in control samples. The average impedance magnitude spectra of lysed HIV and mixture of HIV and EBV was lower than the impedance magnitude spectra of control and EBV samples. There was no significantly difference between average impedance magnitude of control and EBV samples. Control samples were prepared by mixing streptavidin-coated magnetic beads conjugated with anti-gp120 antibodies (Biotin) with 1% Triton X-100 without any viruses in the sample. The viral loads of HIV-1 subtype A and EBV were $1.74 \times 10^8$, $1.9 \times 10^9$, copies/mL, respectively. The viral load of the mixture of HIV and EBV sample was $1.6 \times 10^8$ copies/mL.

FIG. 15A shows impedance magnitude of the PBS/Triton samples with dilution factors between 0.05% to 1%. The impedance magnitude of samples with different dilution factors of PBS and Triton x-100 were measured at 1,000 Hz and 1 V. FIG. 15B shows the impedance magnitude shift measured by 2-probe and 4-probe configurations in the samples with different electrical conductivities. The impedance magnitude change measured in the samples was significantly higher when 4-probe configuration was used compared to 2-probe configuration.

DETAILED DESCRIPTION OF THE INVENTION

Figure 1:
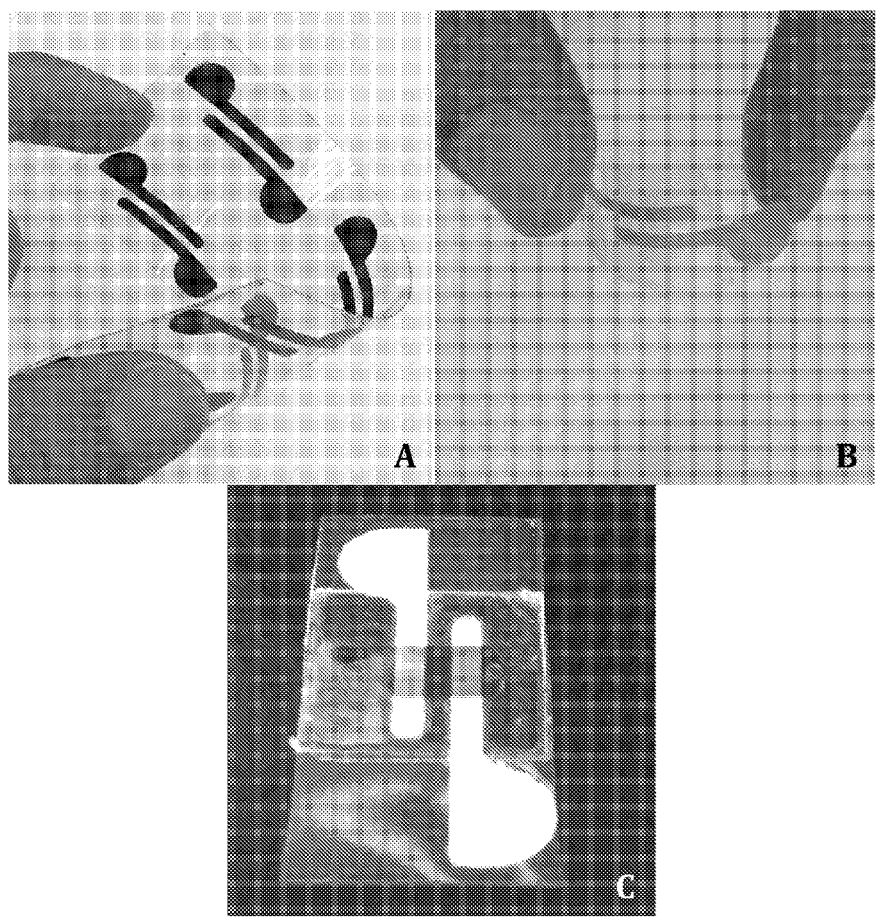
FIGS. 1A and 1B illustrate paper-based microchips with flexible graphite and silver electrodes, respectively.
FIG. 1C illustrates a paper-based microchip with a blood sample filling the channel between the pair of spaced electrodes.
Figure 2:
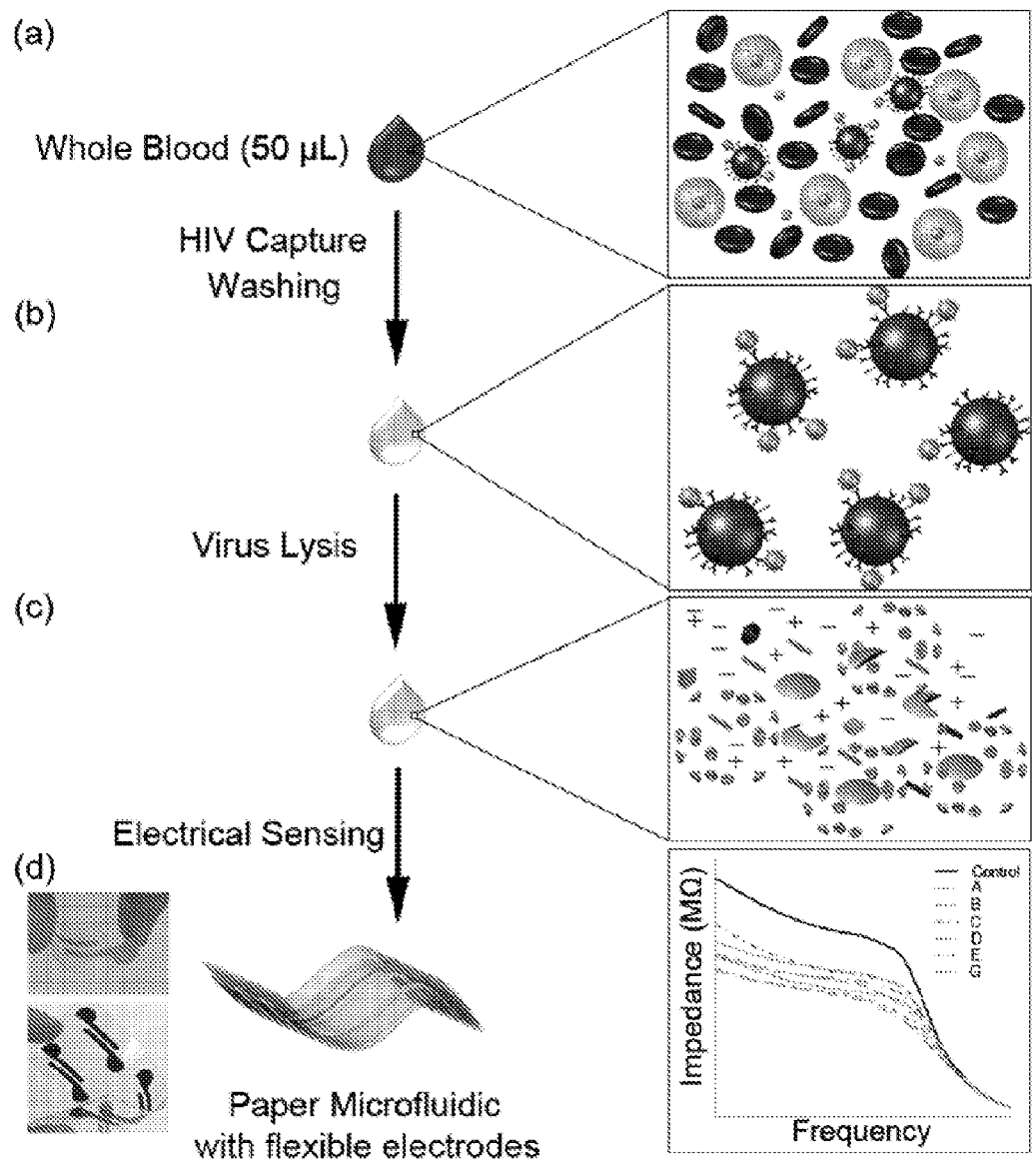
FIG. 2 shows a 3D schematic of the paper-based biosensing system.

Turning now to FIG. 2, the basic process flow for using the paper-based biosensing system to detect HIV-1 subtypes is schematically illustrated according to one exemplary method. In step (a) of the process, the HIV-1 viruses are captured using streptavidin-coated magnetic beads conjugated with gp-120 antibodies in whole blood sample. In step (b), the sample is washed to remove electrically conductive solution. In step (c), the captured viruses are lysed using 1% Triton x-100 to release ions, proteins, antigens, enzymes, and any biomolecules inside the captured viruses. These biomolecules change the electrical conductivity of the solution. In step (d), the viral lysate samples (now fully separated from the magnetic beads) are introduced to the paper-based microfluidic device with silver/graphite electrodes for impedance measurement of the viral lysate samples. An enlarged view of the paper-based microfluidic device is illustrated in FIGS. 1A and 1B, which also illustrates that the paper-based microfluidic device and its electrodes are flexible. The presentation of a blood sample is illustrated in FIG. 1C, in which blood has entered an opening on the top surface of the microfluidic device and has been transported through the channel between the electrodes such that the blood sample runs from one of the electrodes to the other of the electrodes. It is noted that in FIG. 1C, a pair of spaced electrodes are illustrated in a specific configuration. However, it is contemplated that other quantities or arrangements of electrodes or other electrode configurations might be used to measure impedance of a sample. For example, an array of finger electrodes, which are also called interdigitated electrodes, can be used for sensing.

Specific examples are now provided of testing samples using this outlined process and the results thereof. These examples are offered for illustrative purposes only, and are not intended to limit the scope of the present invention in any way. Indeed, various modifications of the invention in addition to those shown and described herein will become apparent to those skilled in the art from the foregoing description and the following example and fall within the scope of the appended claims.

Example I

For the following example, the following reagents were obtained and used. Triton X-100 (100%), glycerol (100%), and Bovin Serum Albumin (BSA, 10%) were purchased from Sigma-Aldrich® (St Louis, Mo.). Dulbecco's Phosphate Buffered Saline (DPBS, 1×) was bought from Life Technologies' (Grand Island, N.Y.). HyPure™ Molecular Biology Grade Water was obtained from Fisher Scientific (Agawam, Mass.). Ethanol (200 proof) was bought from Sigma Aldrich® (Sheboygan, Wis.). Biotinylated polyclonal goat anti-gp120 antibody (4 g/mL) was obtained from Abcam® (Cambridge, Mass.).

Magnetic beads conjugated with anti-gp120 antibodies were prepared. Streptavidin-coated magnetic beads (1 µm diameter) were purchased from Thermo Scientific (Rockford, Ill.). After diluting in DPBS by 1:10 (v/v), the beads were washed three times with DPBS (1.5 mL) using a BioMag® multistep magnetic separator from Polyscience Inc. (Warrington, Pa.). Antibody conjugation was done by adding biotinylated anti-gp120 antibodies with the stock concentration of 15 µg/mL to the magnetic beads solution and incubated for 2 hours at 4° C. on a rotator with a speed of 30 rpm for 2 hours. The non-conjugated antibodies in the solution were then removed from the sample through washing with DPBS (three times).

HIV-1 was then captured on the magnetic beads conjugated with the anti-gp120 antibodies. Multiple HIV-1 subtypes [A, B, C, D, E, G, and panel (A, B, C, D, and circulating recombinant forms, CRF01_AE and CRF02_AG)] were mixed with conjugated magnetic beads and incubated for half an hour at room temperature on a rotator (15 rpm). The viral load of the HIV-1 subtypes in culture media were established to be $1.74 \times 10^8$ (subtype A), $1.2 \times 10^8$ (subtype B), $1.17 \times 10^8$ (subtype C), $2.9 \times 10^8$ (subtype D), $8.39 \times 10^8$ (subtype E), $6.53 \times 10^8$ (subtype G), and $1.48 \times 10^9$ (panel) copies/mL. To prepare the control samples, DPBS solution without viruses was mixed with conjugated magnetic beads.

The mixture of HIV-1 and conjugated magnetic beads were washed four times with 20% glycerol (diluted in grade water) to remove un-captured viruses in the solution and electrically conductive media. After the washing step, 1% Triton-X 100 (diluted in grade water) was mixed with the conjugated magnetic beads and incubated for 5 minutes to lyse the captured viruses. The viral lysis step compromises the membrane of the virus and releases the membrane phospholipids and proteins, capsid proteins, intracellular ions, retroviral enzymes, and nucleic acids into the background solution.

Example II

Microchips were fabricated in the following manner. Two rail electrodes were patterned on hydrophobic transparency papers using silver ink from Engineered Materials Systems, Inc. (Delaware, Ohio). The electrodes geometry and design were cut on a double-sided-adhesive film (DSA) using a VLS2.3 laser cutter from Universal Laser Systems Inc. (Scottsdale, Ariz.). This DSA used as a mask and taped on top of a paper and conductive ink (graphite or silver) was poured on top of the mask to fill the openings on the DSA. A glass cover slip was used to distribute the ink evenly everywhere in the openings. The paper with the inks were then baked in an oven at 80° C. for one hour. After the ink dried, the protective DSA was removed and the electrodes patterned in the openings of the mask were left on the paper. The thickness of the electrodes was approximately 50 µm. The width and spacing of these two rail electrodes were 2 mm and 1 mm, respectively.

Figure 7:
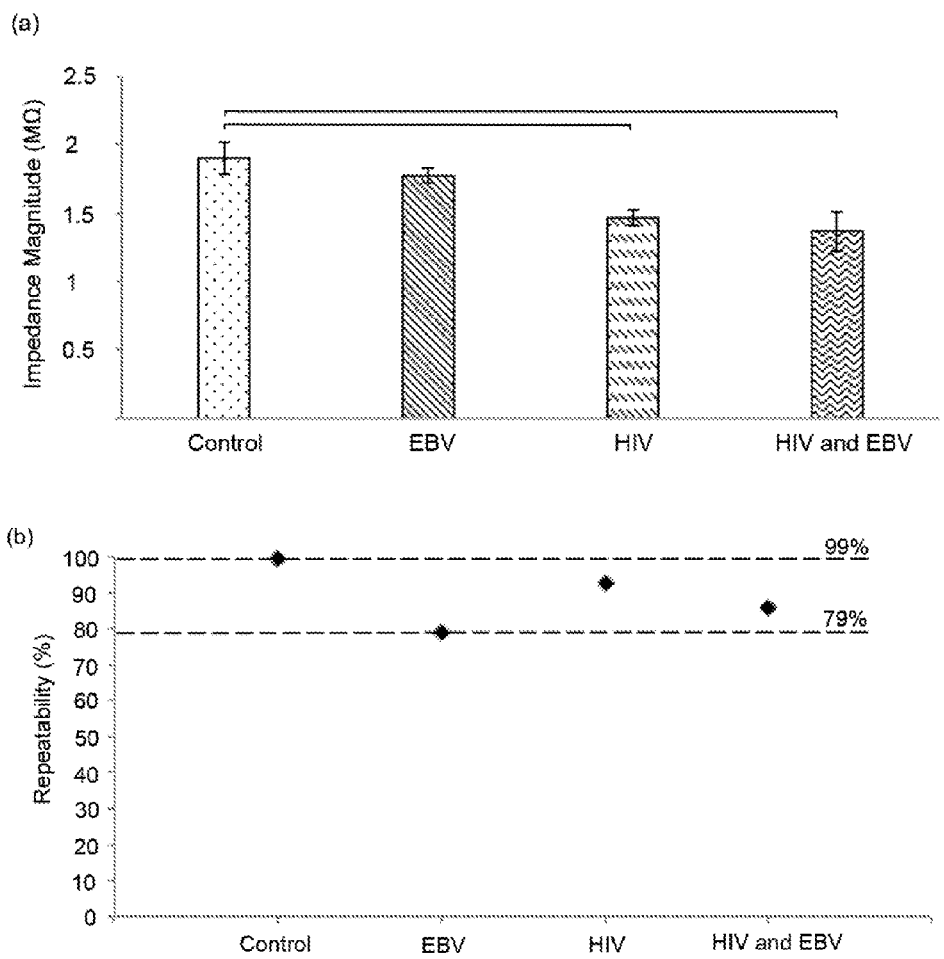
FIG. 7A illustrates the impedance magnitude of the lysed HIV-1 subtype A, EBV, and mixture of HIV and EBV samples at 1,000 Hz and 1 V. Error bars represent standard deviation of the mean (n=3). Brackets connecting individual groups indicate statistically significant impedance magnitude. Statistical significance threshold was set at 0.05, p<0.05.
FIG. 7B illustrates repeatability of the measured impedance magnitude for control, HIV-1 subtype A, EBV, and mixture of HIV and EBV samples. The minimum repeatability that calculated for these measurements was 79%.
Figure 10:
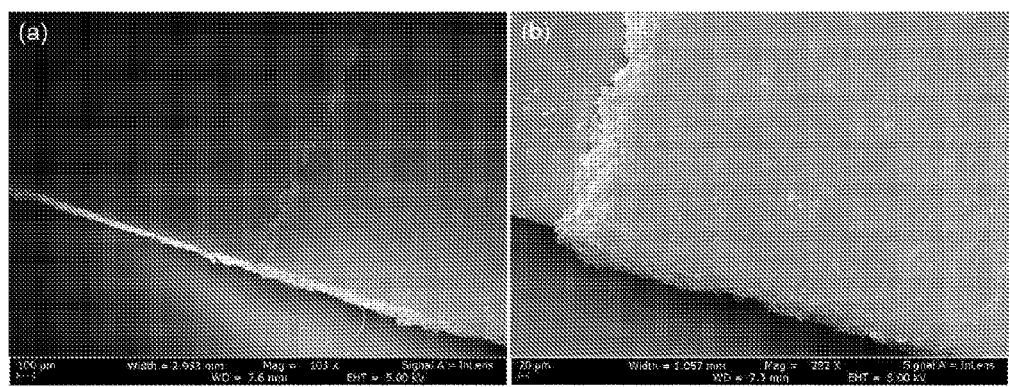
FIG. 10 shows Scanning Electron Microscopy (SEM) images of silver electrodes on paper-based microfluidic devices. SEM images were taken at 5 KV accelerating voltage and 7.6 mm working distance in FIG. 10A, and 7.3 mm working distance in FIG. 10B. Magnification was 103× in FIG. 10 A and 282× in FIG. 10B and signal was InLens.

FIG. 10 shows Scanning Electron Microscopy (SEM) images of silver electrodes on the paper-based microfluidic devices. SEM images were taken at 5 KV accelerating voltage and 7.6 mm working distance in FIG. 10A, and 7.3 mm working distance in FIG. 10B. Magnification was 103× in FIG. 10 A and 282× in FIG. 10B and signal was InLens.

Example III

For the results that follow, Tukey's post-hoc test [Analysis of Variance (ANOVA)] was used to analyze the experimental results for multiple comparisons and the statistical significance threshold was set at 0.05 (n=3, p<0.05), unless otherwise indicated. Statistical analyses were performed with Minitab software (V14, Minitab Inc., State College, Pa., USA).

Example IV

The viral lysate samples were introduced into the paper-based microfluidic device with two rail electrodes.

To detect the captured HIV-1, the impedance magnitude and phase spectra were evaluated for viral lysate samples of multiple HIV subtypes including A, B, C, D, E, G, and panel over a range of frequencies between 100 Hz and 1 MHz at 1 V.

Figure 3:
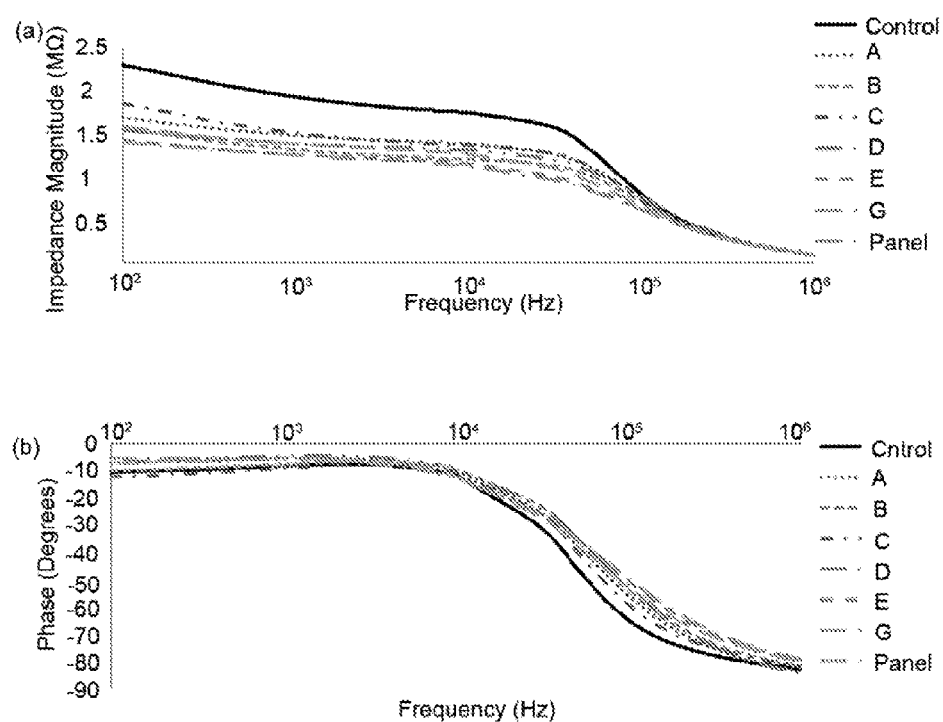
FIG. 3A illustrates impedance magnitude and FIG. 3B illustrates phase spectra of lysed HIV-1 subtypes (subtypes A, B, C, D, E, G, and panel) for frequencies between 100 and 1 MHz measured in the paper-based microfluidic device. Control samples were prepared by mixing streptavidin-coated magnetic beads conjugated with anti-gp120 antibodies (Biotin) with 1% Triton X-100 without any viruses in the sample. The viral loads of HIV-1 subtypes A, B, C, D, E, G, and the panel were $1.74 \times 10^8$, $1.2 \times 10^8$, $1.17 \times 10^8$, $2.9 \times 10^8$, $8.39 \times 10^8$, $6.53 \times 10^8$, and $1.49 \times 10^9$ copies/mL, respectively.

These results are illustrated in FIGS. 3A and 3B. The impedance magnitude spectra of the viral lysate samples for all HIV subtypes were below the impedance magnitude spectra of the control samples for frequencies between 100 Hz and 100 kHz. The impedance magnitude of the viral lysate samples for frequencies above 100 kHz was same as the impedance magnitude of the control samples. Control samples were prepared by mixing DPBS and conjugated magnetic beads without HIV. Impedance phase spectroscopy of the viral lysate samples was same as control samples. The maximum impedance magnitude shift for all HIV subtypes with respect to control samples was observed to occur at 1,000 Hz. Therefore, this frequency was chosen to further statistically compare the impedance magnitude results.

Figure 4:
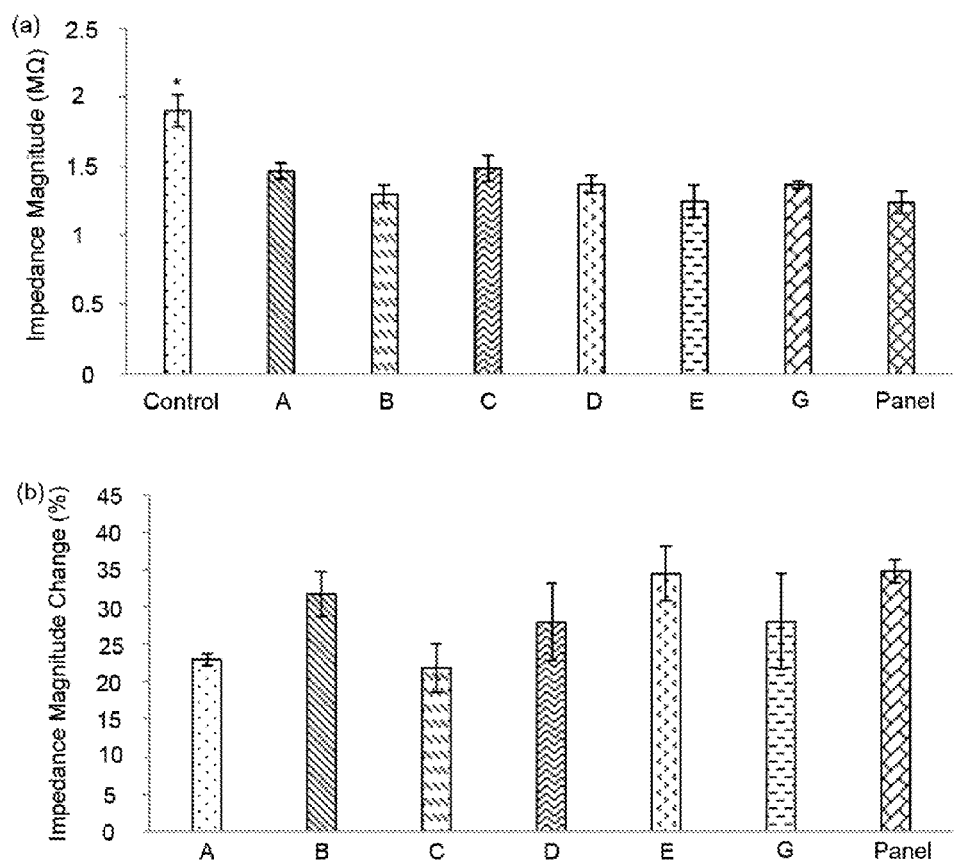
FIG. 4A illustrates impedance magnitude of HIV-1 lysate samples (subtypes A, B, C, D, E, G, and panel) at 1,000 Hz and 1 V.
FIG. 4B illustrates normalized impedance magnitude change of HIV-1 lysate samples with respect to control samples. There was no virus in control samples, which was prepared by mixing the streptavidin-coated magnetic beads conjugated with anti-gp120 antibodies (Biotin) with 1% Triton X-100. "*" indicates statistically significant impedance magnitude change compared to all other groups. Statistical assessment on the results was performed using ANOVA with Tukey posthoc test for multiple comparisons. Statistical significance threshold was set at 0.05, p<0.05. Error bars represent standard deviation of the mean (n=3). The viral loads of these HIV-1 subtypes were $1.74 \times 10^8$, $1.2 \times 10^8$, $1.17 \times 10^8$, $2.9 \times 10^8$, $8.39 \times 10^8$, $6.53 \times 10^8$, and $1.49 \times 10^9$ copies/mL for subtypes A, B, C, D, E, G, and panel, respectively.

FIG. 4A shows the impedance magnitude of the viral lysate samples as well as control sample at 1,000 Hz and 1 V. The impedance magnitudes of the viral lysate samples were significantly lower than the impedance magnitude of the control sample (n=3, p<0.05). No significant difference was observed between the impedance magnitudes of multiple HIV subtypes (n=3, p>0.05). The impedance magnitude of the viral lysate samples were also normalized with respect to the impedance magnitude of control sample at 1,000 Hz as shown in FIG. 4B. The impedance magnitude shifts for HIV-1 subtypes A, B, C, D, E, G, and panel were 23±3, 32±3, 22±5, 28±3, 34±6, 28±1, 35±4, respectively.

These results show the ability of the paper-based microchip to detect multiple HIV-1 subtypes spiked in DPBS at viral loads around $10^8$ copies/mL.

Example V

Figure 5:
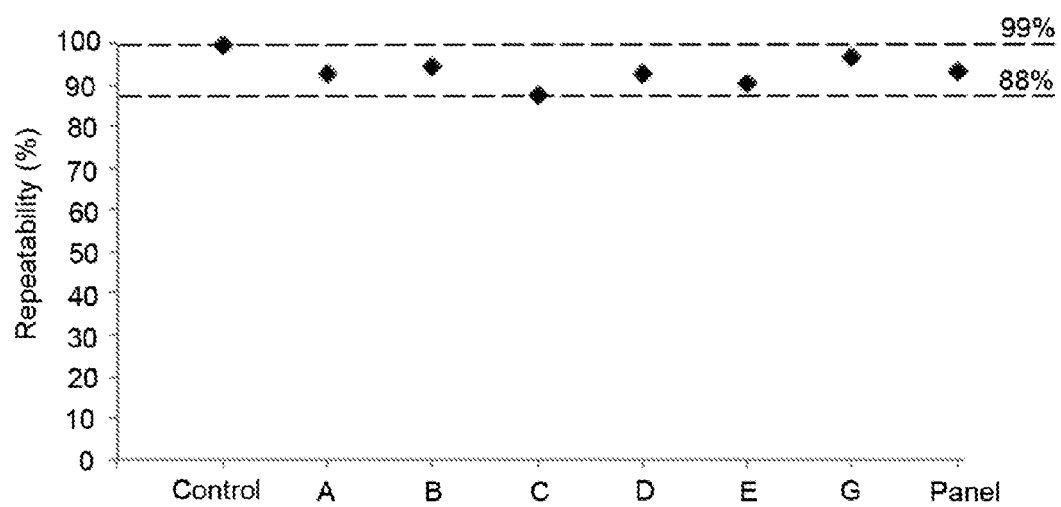
FIG. 5 illustrates the repeatability of the measured impedance magnitude for HIV-1 subtypes A, B, C, D, E, G, and panel. The minimum repeatability that calculated for these measurements was 88%.

The repeatability of these electrical sensing measurements were evaluated following the repeatability definition:

$$\text{Repeatability} = \frac{I.M. \text{ change mean}}{I.M. \text{ change mean} + \text{standard error of measurement}} \times 100$$

in which "I.M." is the impedance magnitude of the viral lysate sample or control sample. As illustrated in FIG. 5, the repeatability of the impedance magnitude measurement for control sample and viral lysate samples were between 88% and 99%.

Example VI

Figure 6:
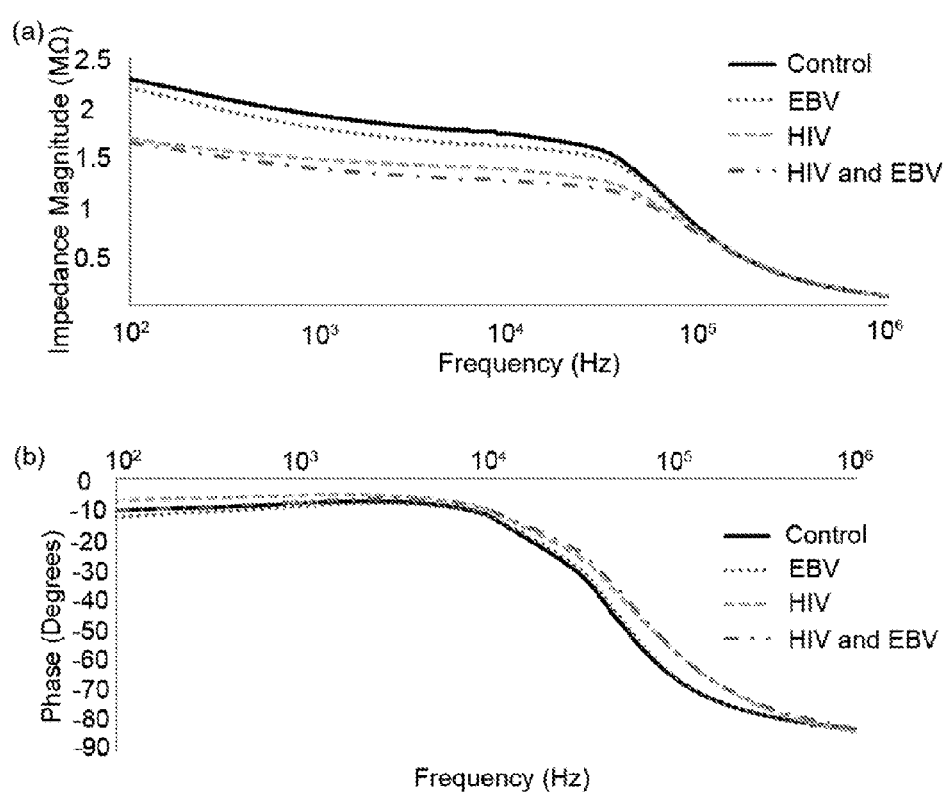
FIGS. 6A and 6B show a specificity evaluation of the paper-based microchip device.

The specificity of the paper-based microchip for HIV-1 detection was also evaluated in the presence of Epstein-Barr virus (EBV) as a virus model. The impedance magnitude (FIG. 6A) and phase spectra (FIG. 6B) of the HIV, EBV, and the mixture of HIV and EBV samples were measured and compared with control samples where there was no virus in the sample. As FIGS. 6A and 6B illustrate, the impedance phase spectra of all the samples were the same; however, the impedance magnitude of the HIV and the mixture of HIV and EBV samples were lower compared to control samples. The impedance magnitude spectra of EBV samples was not significantly lower than control samples.

Based on the previous tests, 1,000 Hz was chosen as a single frequency for impedance magnitude comparison between the samples as maximum impedance magnitude shift was observed at this frequency.

FIG. 7A illustrates that the impedance magnitude of HIV and the mixture of HIV and EBV samples were significantly different compared to control samples at 1,000 Hz. The impedance magnitude of HIV and the mixture of HIV and EBV was not significantly different (n=3, p>0.05).

The repeatability of these impedance magnitude measurements were also evaluated and measured. As illustrated in FIG. 7B, the repeatability of the experimental measurements was between 79% and 99%.

These results evidence the ability of the microchip to selectively detect HIV-1 in the presence of another type of virus.

Example VII

Figure 8:
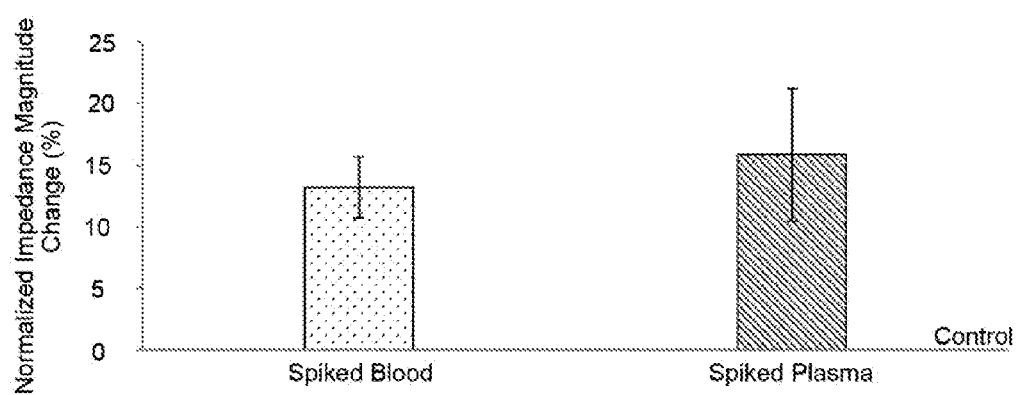
FIG. 8 shows normalized impedance magnitude change of HIV-1 lysate samples with respect to control samples at 1,000 Hz and 1 V in spiked blood and plasma samples. There was no virus in control samples, which was prepared by mixing the streptavidin-coated magnetic beads conjugated with anti-gp120 antibodies (Biotin) with 1% Triton X-100. Statistical assessment on the results was performed using ANOVA with Tukey posthoc test for multiple comparisons. Statistical significance threshold was set at 0.05, p<0.05. Error bars represent standard deviation of the mean (n=3). The viral loads of the HIV-1 subtype C used here was $1.17 \times 10^8$.

FIG. 8 shows normalized impedance magnitude change of HIV-1 lysate samples with respect to control samples at 1,000 Hz and 1 V in spiked blood and plasma samples. There was no virus in control samples, which was prepared by mixing the streptavidin-coated magnetic beads conjugated with anti-gp120 antibodies (Biotin) with 1% Triton X-100.

Statistical assessment on the results was performed using ANOVA with Tukey posthoc test for multiple comparisons. Statistical significance threshold was set at 0.05, p<0.05. Error bars represent standard deviation of the mean (n=3). The viral loads of the HIV-1 subtype C used here was $1.17 \times 10^8$.

These results indicate that the method described above could be used to detect HIV-1 in either blood or plasma.

Example VIII

To establish that HIV-1 was in fact captured on the surface of the streptavidin-coated magnetic beads conjugated with biotinylated anti-gp120 antibodies, HIV-1 was tagged with a green fluorescent protein (GFP) and captured on the beads.

Figure 9:
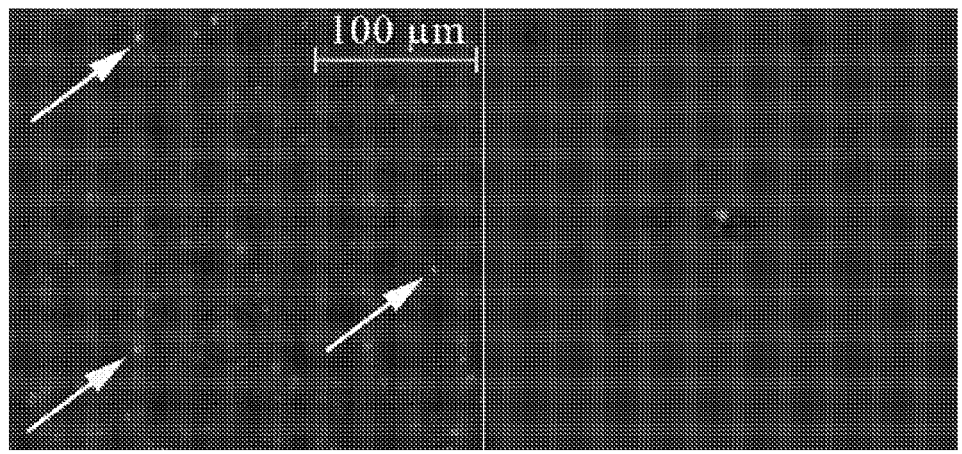
FIG. 9 shows fluorescent images of GFP tagged HIV-1 captured on the surface of the streptavidin-coated magnetic beads conjugated with biotinylated anti-gp120 antibody taken using a 10× objective lens.

FIG. 9 shows fluorescent images of green fluorescent protein (GFP) tagged HIV-1 captured on the surface of the streptavidin-coated magnetic beads conjugated with biotinylated anti-gp120 antibody taken using a 10× objective lens. Because the images in the application are only in black and white, arrows have been used to indicate the areas that appeared green in the image.

Example IX

Figure 11:
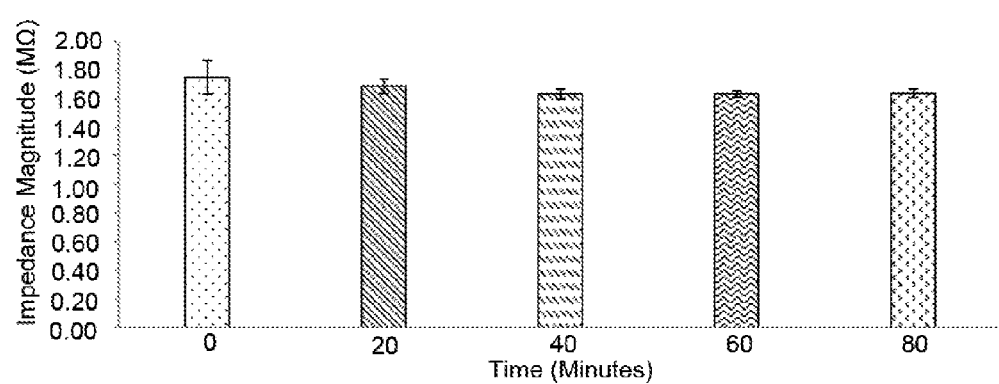
FIG. 11 shows the effect of time on the impedance magnitude of Triton x-100. Impedance magnitude of 1% Triton x-100 samples were measured at 1,000 Hz and 1 V every 20 minutes for 80 minutes. Statistical assessment on the results was performed using ANOVA with Tukey posthoc test for multiple comparisons. Statistical significance threshold was set at 0.05, p<0.05. There was no significant difference between the impedance magnitudes of the samples over the 80 minutes period (n=3, p>0.05).

The impedance magnitude of Triton x-100 Was measured over time to ensure that the impedance magnitude of Triton x-100 did not vary with time (as such a relationship, if significant, could raise issues relating to the confidence with which the viral samples were detected). FIG. 11 shows the effect of time on the impedance magnitude of Triton x-100. Impedance magnitude of 1% Triton x-100 samples were measured at 1,000 Hz and 1 V every 20 minutes for 80 minutes.

Statistical assessment on the results was performed using ANOVA with Tukey posthoc test for multiple comparisons. Statistical significance threshold was set at 0.05, p<0.05.

There was no significant difference between the impedance magnitudes of the samples over the 80 minutes period (n=3, p>0.05).

Example X

Further trials were run to establish whether the change in impedance magnitude observed above in blood was similarly observable in plasma.

Figure 12:
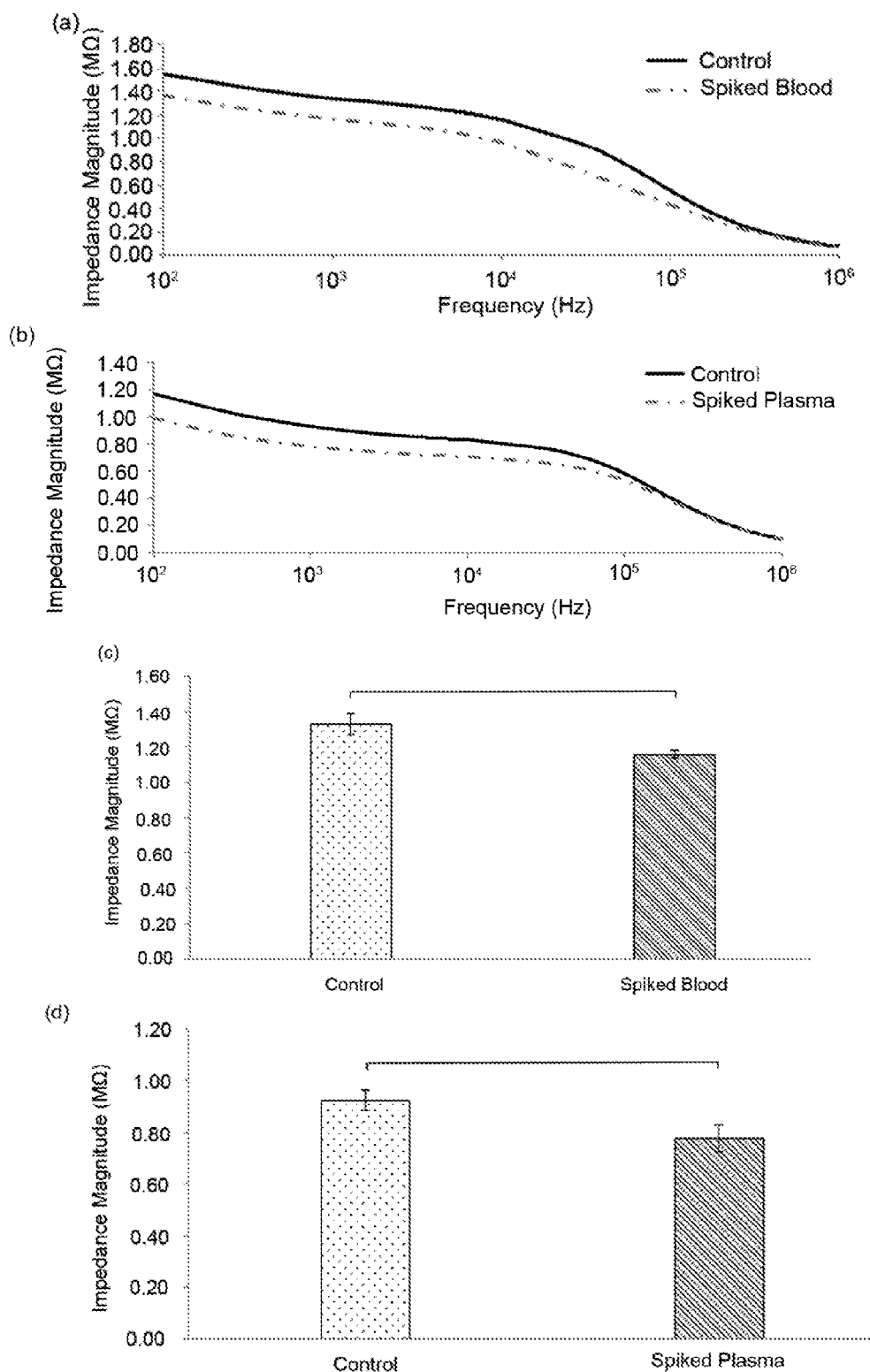
FIG. 12 shows average impedance magnitude spectra of control samples and lysed HIV-1 subtype C ($1.17 \times 10^8$) spiked in blood in FIG. 12A and plasma in FIG. 12B for frequencies between 100 and 1 MHz. Control samples were prepared by mixing streptavidin-coated magnetic beads conjugated with anti-gp120 antibodies (Biotin) with 1% Triton X-100 without any viruses in the sample. Average impedance magnitude of control and HIV-1 subtype C lysate spiked in blood is shown in FIG. 12C and plasma in FIG. 12D at 1,000 Hz and 1 V. Error bars represent standard deviation of the mean (n=3). Brackets connecting individual groups indicate statistically significant impedance magnitude difference. Statistical significance threshold was set at 0.05, p<0.05.

FIG. 12A shows the average impedance magnitude spectra of control samples and lysed HIV-1 subtype C (viral load of $1.17 \times 10^8$) spiked in blood for frequencies between 100 and 1 MHz and FIG. 12 B shows average impedance magnitude spectra of control samples and lysed HIV-1 subtype C ($1.17 \times 10^8$) spiked in blood for frequencies between 100 and 1 MHz. Control samples were prepared by mixing streptavidin-coated magnetic beads conjugated with anti-gp120 antibodies (Biotin) with 1% Triton X-100 without any viruses in the sample.

The average impedance magnitude of control and HIV-1 subtype C lysate spiked in blood is shown in FIG. 12C and plasma in FIG. 12D at 1,000 Hz and 1 V. Error bars represent standard deviation of the mean (n=3). Brackets connecting individual groups indicate statistically significant impedance magnitude difference. The statistical significance threshold was set at 0.05, p<0.05.

These results indicate that there was a statistically significant difference between the impedance magnitude of the control blood samples and the blood samples spiked with HIV-1 and a statistically significant difference between the impedance magnitude of the plasma control samples and the plasma samples spiked with HIV-1

Example XI

Figure 13:
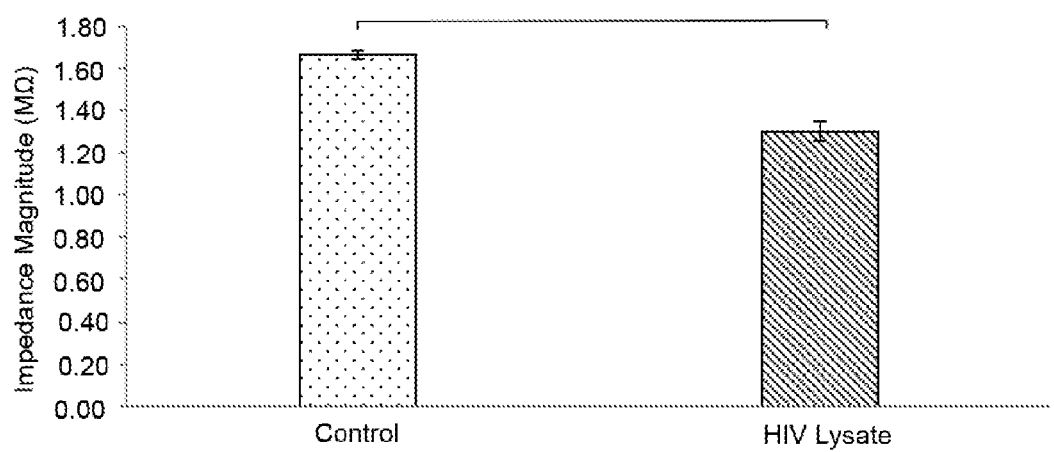
FIG. 13 illustrates the average impedance magnitude of the HIV-1 lysate (subtype D) with viral load of $2.9 \times 10^6$ copies/mL at 1,000 Hz and 1 V. The sample volume was increased to 5 mL for this virus concentration to generate a detectable impedance magnitude change compared to control samples. Error bars represent standard deviation of the mean (n=3). Brackets connecting individual groups indicate statistically significant impedance magnitude. Statistical significance threshold was set at 0.05, p<0.05.

FIG. 13 illustrates the average impedance magnitude of the HIV-1 lysate (subtype D) with viral load of $2.9 \times 10^6$ copies/mL at 1,000 Hz and 1 V. The sample volume was increased to 5 mL for this virus concentration to generate a detectable impedance magnitude change compared to control samples. Error bars represent standard deviation of the mean (n=3). Brackets connecting individual groups indicate statistically significant impedance magnitude. Statistical significance threshold was set at 0.05, p<0.05.

Example XII

Figure 14:
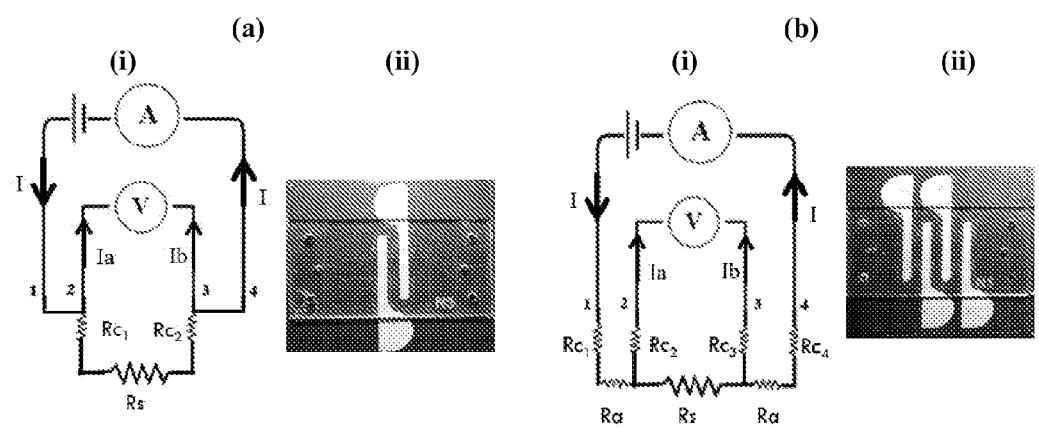
FIG. 14 illustrates equivalent electronic circuit and microchips with (a) a 2-probe electrode configuration and (b) a 4-probe electrode configuration.

Electrode geometry and configuration may have a significant impact on the electrical sensing method to detect and quantify HIV viral lysate. In FIG. 14, two microchip designs are illustrated which are subsequently used to demonstrate the effect of microchip designs with different electrode configurations (2-probe vs. 4-probe) on the impedance spectroscopy of samples with various electrical conductivities. FIG. 14(a)(ii) shows 2-probe electrode configuration and FIG. 14(a)(i) shows the equivalent electronic circuit used for testing. FIG. 15(a)(ii) shows 4-probe electrode configuration and FIG. 15(a)(i) shows the equivalent electronic circuit used for testing.

Impedance measurement using the 2-probe configuration takes into account the contact resistance ($R_C$) between the electrode and the sample in microchannel, whereas the 4-probe configuration eliminates the effect of contact resistance in impedance measurement on-chip. Contact resistance can play a major role in impedance analysis specifically when the electrical conductivity of the sample is low. In the HIV lysate impedance measurements the conductivity is as low as 20 to 200 μS/cm, therefore the contact resistance in our measurements would be high. Impedance of the 2-probe configuration is equal to $R_s+R_{C1}+R_{C2}$, whereas the impedance magnitude of the system in 4-probe configuration is equal to $R_S$.

Figure 15:
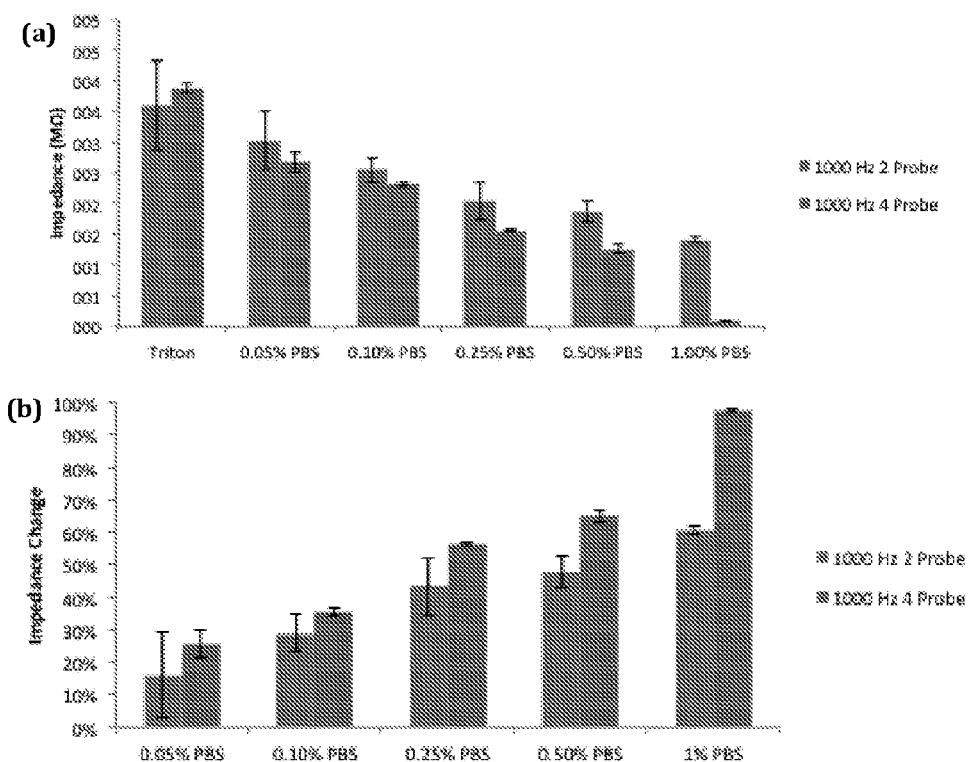
FIG. 15 illustrates impedance measurement results using the 2-probe and 4-probe electrode configurations.

With reference to FIG. 15, the experimental results demonstrated that the 4-probe configuration showed a higher impedance magnitude change in PBS samples with different dilution factors when it is mixed with Triton x-100. The impedance magnitude of 1% Triton x-100 was 3.59 and 3.87 MΩ, when it was measured with 2-probe and 4-probe configurations, respectively. The impedance magnitude of Triton x-100 mixed with PBS at 1% v/v dilution factor was 1.41 and 0.89 MΩ, when it was measured with 2-probe and 4-probe configurations, respectively.

The present invention has been described in terms of one or more preferred embodiments, and it should be appreciated that many equivalents, alternatives, variations, and modifications, aside from those expressly stated, are possible and within the scope of the invention.

We claim:

1. A method of detecting a pathogen in a sample, the method comprising:
    capturing the pathogen from the sample with at least one recognition element on a substrate of a paper-based microfluidic device;
    washing the sample to remove electrically conductive solution;
    lysing the pathogen to release at least one electrically conductive chemical entity inside the pathogen; and
    measuring an impedance magnitude of the sample across a pair of spaced electrodes comprising silver and disposed on the paper-based microfluidic device to detect a presence of the pathogen in the sample.

2. The method of claim 1, wherein the sample is blood or plasma, the pathogen is a virus, and the at least one recognition element is an antibody.

3. The method of claim 1, wherein the at least one chemical entity comprises one or more of ions, proteins, antigens, enzymes, and biomolecules inside the captured pathogen.

4. The method of claim 1, wherein Triton x-100 is used to lyse the pathogen to release at least one electrically conductive chemical entity inside the pathogen.

5. The method of claim 1, wherein measuring an impedance magnitude of the sample to detect the presence of the pathogen in the sample includes measuring an impedance magnitude of a control sample, measuring the impedance magnitude of the sample and determining the change in impedance magnitude from the control sample to the sample to detect the presence of the pathogen in the sample.

6. The method of claim 1, wherein the impedance magnitude is measured at 1000 Hz and 1 V.

7. The method of claim 1, wherein detection of the pathogen includes the ability to selectively detect the pathogen in the presence of another type of pathogen.

8. The method of claim 1, wherein the paper-based microfluidic device having the pair of spaced electrodes disposed thereon has a microfluidic channel spanning the distance between the pair of spaced electrodes.

* * * * *